United States Patent [19]
Scott et al.

[11] Patent Number: 5,395,455
[45] Date of Patent: Mar. 7, 1995

[54] PROCESS FOR THE PRODUCTION OF ANHYDROSUGARS FROM LIGNIN AND CELLULOSE CONTAINING BIOMASS BY PYROLYSIS

[75] Inventors: Donald S. Scott; Jan Piskorz; Desmond Radlein; Piotr Majerski, all of Waterloo, Canada

[73] Assignee: Energy, Mines and Resources - Canada, Ottawa, Canada

[21] Appl. No.: 29,418

[22] Filed: Mar. 9, 1993

[30] Foreign Application Priority Data

Mar. 10, 1992 [GB] United Kingdom .................. 9205143
Mar. 16, 1992 [GB] United Kingdom .................. 9205713

[51] Int. Cl.$^6$ .......................... C13K 1/02; C07G 17/00
[52] U.S. Cl. ........................................ 127/37; 536/124
[58] Field of Search ................... 127/37; 536/127, 124

[56] References Cited

U.S. PATENT DOCUMENTS

| | | | |
|---|---|---|---|
| Re. 12,069 | 12/1902 | Classen | 127/37 |
| Re. 12,108 | 5/1903 | Classen | 127/37 |
| 654,518 | 7/1900 | Classen | 127/37 |
| 707,903 | 8/1903 | Classen | 127/37 |
| 745,675 | 12/1903 | Roth | 127/37 |
| 985,725 | 2/1911 | Cohoe | 127/37 |
| 985,726 | 2/1911 | Cohoe | 127/37 |
| 2,697,702 | 12/1954 | Heritage et al. | 162/16 |
| 3,309,355 | 3/1967 | Heritage et al. | 536/128 |
| 3,309,356 | 3/1967 | Esterer | 536/127 |
| 3,374,222 | 3/1968 | Peniston | 536/127 |
| 3,776,897 | 12/1973 | Ikari et al. | 536/127 |
| 3,875,317 | 4/1975 | Ferguson | 99/2 |
| 4,137,395 | 1/1979 | Buck et al. | 536/1 |
| 4,281,063 | 7/1981 | Tsao et al. | 127/37 |
| 4,351,905 | 9/1982 | Clyde | 435/316 |
| 4,468,256 | 8/1984 | Hinger | 127/1 |
| 4,880,473 | 11/1989 | Scott et al. | 127/37 |
| 4,956,458 | 9/1990 | Luo et al. | 536/112 |
| 5,023,330 | 6/1991 | Gander et al. | 536/124 |
| 5,046,514 | 9/1991 | Bolt | 131/359 |
| 5,188,673 | 2/1993 | Clausen et al. | 127/37 |
| 5,252,188 | 10/1993 | Stradal et al. | 203/43 |
| 5,270,067 | 12/1993 | Underwood et al. | 426/138 |

Primary Examiner—David M. Naff
Assistant Examiner—Mike Meller

[57] ABSTRACT

A process is described for the production of anhydrosugars such as levoglucosan (1,6-anhydro-$\beta$-D-glucopyranose), from liquids obtained by the fast thermal pyrolysis of pretreated lignocellulosics or celluloses. In this process, the pyrolytic liquids containing the anhydrosugars are produced with a substantially reduced amount of lignin-derived components by using as feedstock materials which have been previously delignified and then pretreated, or by preferential oxidation of the lignin fraction of a pretreated biomass during pyrolysis. The preparation from pretreated biomass of pyrolytic liquors from which the lignin derived chemical products of fast pyrolysis are absent or in low concentrations permits simpler and more economical recovery of crystalline levoglucosan and other anhydrosugars, or a more economical preparation of readily fermentable aqueous sugar solutions therefrom. A new procedure for the recovery of crystalline levoglucosan from such solutions is described.

19 Claims, 3 Drawing Sheets

PROCESS FOR THE PRODUCTION OF ANHYDROSUGARS FROM LIGNIN AND CELLULOSE CONTAINING BIOMASS BY PYROLYSIS

BACKGROUND OF THE INVENTION

This invention relates to an improved process for the production of sugars and anhydrosugars from biomass materials such as wood or other lignocellulosics, or from biomass derived materials as newsprint or other paper goods, wood pulps, waste fibre etc.

Scott & Pisorz U.S. Pat. No. 4,880,473 discloses a process for preparation of solutions of fermentable sugars using a fast pyrolysis of pretreated biomass. In that invention, the pretreatment was a dilute acid prehydrolysis which removed the majority of the hemicellulose fraction as well as the alkali and alkaline earth cations associated with the biomass. As a result, as much as 80% of the lignin appeared in the pyrolysis liquid as pyrolytic lignin, i.e. the volatile decomposition products primarily derived from the lignin fraction of biomass. A portion of these lignin-derived compounds can be separated by water extraction from the more soluble sugars and anhydrosugars derived from the cellulose fraction, and which are recovered in the aqueous phase.

It is well known that the alkaline cations associated with the biomass act to promote certain thermal decomposition reactions, in particular those reactions which lead to char or gas production. These cations are known to be able to be removed by treatment with very dilute acid at normal temperatures, such that the lignin, hemicellulose and cellulose fractions of the biomass are substantially unaffected. The resulting deionized biomass differs from that given a prehydrolysis pretreatment in that the hemicellulose content is retained in the solid pretreated lignocellulose.

The behaviour of deionized wood has been shown in laboratory batch pyrolysis reactions carried out at very small scale under vacuum with slow heating to be different from that of normal wood. The removal of the cations enhanced the yield of anhydrosugars derived from cellulose, and particularly increased the yield of anhydroglucose, (levoglucosan). Typically, deionization was carried out by batch-wise contacting of the wood with very dilute acid, for example 0.1% sulfuric or hydrochloric acid, and then washing it thoroughly with distilled or deionized water to remove the reagent. The deionized wood was then pyrolyzed under vacuum in microscale laboratory batch reactors in the absence of air or oxygen. Much poorer yields of levoglucosan were obtained from these batch reactions when carried out at atmospheric pressure. Sugars or anhydrosugars derived from the pyrolysis of the hemicellulose fraction have apparently not previously been reported as products obtained from fast pyrolysis of deionized lignocellulosics. This suggests that at the laboratory conditions used in earlier work of others, thermal fragmentation of the hemicelluloses predominated over depolymerization reactions.

Other methods of converting cellulose to fermentable sugars, mainly glucose, are carried out in the liquid phase and require digestion in acid. If this digestion is done using a strong acid, many undesirable and toxic side products are formed. If weak acid is used, poorer glucose yields and more dilute solutions are obtained. In this context, it is also known to use a weak acid treatment to prehydrolyze cellulosic raw material followed by enzymatic hydrolysis. This procedure can yield an improved product at higher concentrations compared to weak acid hydrolysis above. However this process is relatively complex and expensive. Other liquid phase methods such as those known as steamexplosion, may also be cited, for example in Hinger, U.S. Pat. 4,468,256 where glucose is produced from vegetable raw material by impregnating the raw material with dilute acid and subsequent heating to a temperature of above 250° C. by means of high pressure steam. This heating step takes place in a short time accompanied by a sudden pressure rise. In these liquid phase acid digestion methods the principal product from the cellulose is glucose, and anhydrosugars such as levoglucosan are largely absent.

A pyrolysis process for the production of levoglucosan from wood has been described in Esterer U.S. Pat. No. 3,309,356 and in Peniston U.S. Pat. No. 3,374,222. These processes did not use any pretreatment of the wood but stated that it was unnecessary. Also, the pyrolysis process used gave a two-phase liquid. Further, the relatively long residence time of the condensable volatiles in the reactor, approximately 15 seconds, would reduce significantly the possible yields obtainable. In the above Esterer patent it was necessary to remove the lignin-derived material soluble in the aqueous phase by a solvent extraction procedure. In the Peniston patent, these materials as well as carbohydrate derived acids were removed by conversion to insoluble metal salts.

The oxidation of biomass materials in air or oxygen has been very extensively studied in combustion and gasification processes. In particular, the effect of added cations or of the indigenous cations of the wood on the combustion behaviour has been widely reported in connection with fire studies. The indigenous alkaline cations such as K, Ca, Na, Mg or additions of these cations are well known to be effective gasification catalysts in air or oxygen blown systems. Fast pyrolysis with added air to produce liquids and char from biomass has been reported as part of the LEBEN program in Italy, carried out under the sponsorship of the European Economic Community. In general, use of air or oxygen in the fast pyrolysis of biomass results in reduced liquid yields (20-40% vs. 50-80% for non-oxidative pyrolysis) and in degradation of the product in terms of yields of specific desirable chemicals.

There is a need for a more economic process for the deionization of wood or other biomass or biomass-derived materials for the purpose of carrying out a fast pyrolysis process for the conversion by thermal means of cellulose or hemicellulose to sugars and anhydrosugars, and which would allow these processes to become competitive with other processes for the conversion of cellulose or hemicellulose to anhydrosugars or fermentable sugars. Improvements in the fast pyrolysis process would also be valuable in reducing the cost of this method of conversion of hemicellulose or cellulose to sugars or anhydrosugars.

SUMMARY OF THE INVENTION

According to the invention there is provided a process for the treatment of biomass, including lignocellulosic materials, or products derived from biomass, which contain cellulose, hemicellulose and lignin fractions as major components in widely variable amounts depending on whether the material is, for example, natural wood or bark, an agricultural product or residue, or a product (such as paper) or residue of a manufacturing process for biomass (such as pulping, extraction, etc.). In this process alkali and alkaline earth cations are removed from the biomass to allow an enhanced conversion of the cellulose and hemicellulose fractions to various anhydrosugars or sugars in a fast thermal pyrolysis process. Further, the pyrolytic liquids containing levoglucosan and other anhydrosugars as major components are produced with a low to zero content of lignin-derived compounds, which simplifies and makes more economical the recovery of levoglucosan and other anhydrosugars, or the preparation of concentrated aqueous solutions of fermentable sugars.

Thus, one feature of the present invention is a process for the production of anhydrosugars from cellulose-containing biomass comprising the following steps: (a) treating cellulose-containing biomass with a dilute acid at a concentration whereby alkali and alkaline earth cations are removed from the biomass while cellulose and hemicellulose are not dissolved, (b) separating a cellulose and hemicellulose-containing solid phase, (c) subjecting the resulting solid phase to rapid pyrolysis at atmospheric pressure and at a temperature in the range of 400° C. to 650° C. and a residence time of pyrolytic vapors of less than 10 seconds, to thereby obtain a crude product containing anhydrosugars and (d) isolating the anhydrosugars as a product.

In an alternative process, the steps comprise: (a) treating lignin and cellulose-containing biomass with a mineral acid having a concentration in the range of 1% to 10% by weight whereby hemicellulose is dissolved and alkali and alkaline earth cations are removed from the biomass while cellulose and lignin are not dissolved, (b) separating a cellulose and lignin-containing solid phase, (c) subjecting the resulting solid phase to rapid pyrolysis at atmospheric pressure, a temperature in the range of 400° C. to 650° C., a residence time of pyrolytic vapors of less than 10 seconds and in the presence of excess oxygen sufficient to completely oxidize lignin contained in the biomass feedstock, to thereby obtain a crude product containing anhydrosugars and (d) isolating the anhydrosugars as a product.

The entire industrial procedure to which the present invention preferably relates comprises the following steps:
 (a) Biomass is treated with a dilute acid capable of replacing cations associated with the biomass with protons (as a general guide requiring an acid with pK values less than about 4.8) and using a sufficient excess of acid to exchange all alkaline cations and sufficient excess solution to displace to a high degree all cation contaminated acid solution.
 (b) In an alternative pretreatment procedure when primarily levoglucosan or glucose derived from cellulose are the desired products, the biomass is contacted with sulfuric acid, 1% to 10% by weight concentration at 70° C. to 100° C. for 2 to 6 hours to solubilize the majority of the hemicellulose content and to remove the alkaline cations, but not the cellulose or lignin fractions (a process known as "prehydrolysis").
 (c) The solid deionized or prehydrolyzed biomass residue is separated from the acid solution, and washing with deionized water, if necessary, or addition of a solution containing an additive.
 (d) The resulting solid deionized biomass residue after drying is subjected to fast pyrolysis under conditions of controlled oxidation to obtain a crude product containing sugars and anhydrosugars, and specifically, levoglucosan as a major component. If the original feed contains little or no lignin, as in bleached pulp or some papers, then oxidative pyrolysis is not necessary, and non-oxidizing pyrolysis atmosphere can be used, if convenient.
 (e) If a solution of anhydrosugars is desired, the aqueous pyrolysis liquid if filtered, if necessary, and treated with activated char as in conventional sugar refining practice. The clarified syrup is then hydrolyzed to glucose or other sugars using dilute acid in well known technology.
 (f) If crystalline levoglucosan or other crystalline anhydrosugars are desired, the majority of the water is removed from the crude pyrolytic liquid by evaporation, preferably under vacuum; by azeotropic distillation; by absorption; or by other means.
 (g) The anhydrous or nearly anhydrous residue obtained in (f) is dissolved in hot alcohol such as methanol, ethanol or propanol, with ethanol as the preferred solvent using an alcohol/residue weight ratio of 0.5 to 2.0.
 (h) The hot alcoholic solution is filtered if necessary, and then treated with activated carbon.
 (i) The purified alcohol solvent is evaporated until the concentration of levoglucosan is in the range of 15% to 30% by weight and is then cooled at a slow controlled rate to form crystals of levoglucosan.
 (j) The levoglucosan crystals are separated from the mother liquor from step (i).
 (k) A further amount of alcohol solvent is evaporated from the mother liquor and by slow controlled cooling a second crop of crystals is obtained.
 (l) Step (k) is repeated until crystals are no longer of sufficient purity with respect to levoglucosan content.
 (m) Crystals of other anhydrosugars may be recovered from the residual mother liquor by well-known techniques of fractional crystallization and further purified if necessary by recrystallization from pure alcohol, preferably ethanol.

Suitable acids for deionizing the biomass include sulfuric acid and other mineral acids such as hydrochloric or sulfurous acid, or organic acids of sufficiently low pK values, for example, about 4.8 or less. For sulfuric acid, concentrations in the range of 0.01 to 1.0%, preferably 0.05 to 0.5% by weight are satisfactory with a concentration of 0.1% being very suitable. For weak organic acids, such as acetic acid, somewhat higher concentrations are required to give a performance which is equivalent to 0.1% sulfuric acid. A suitable concentration can be estimated from the dissociation constants of the acid relative to sulfuric acid. The time of treatment depends to some extent on the particle size of the biomass, its physical structure and the temperature of the treatment. For wood particles of 0.5 mm size at room temperature with 0.1% sulfuric acid, a batch solid-continuous liquid flow percolation techniques was used to give an excess acid amount of over 100% at a treatment rate of 0.002 m3/kg h. At higher temperatures or for smaller particle sizes this treatment time could be considerably reduced inasmuch as the time required depends on the acid and cation transfer rates into and out of the biomass solid structure. For example, a steam exploded wood in which the biomass structure has been made much more easily accessible to mass transfer could be treated in a much shorter time.

A continuous displacement technique is preferred for deionization because the utilization of the acid is more efficient and because the displacement of the cation containing solution can be more efficiently done. It is a novel element of this invention that a percolation technique through a bed of biomass particles has been used successfully to result in a much more economical use of extraction acid and to minimize equipment costs and complexity. Of course, multistage countercurrent extraction stages could also be used but costs would be higher for this mode of processing. In known systems in which only small laboratory batches of biomass have been deionized, it was not necessary to minimize costs of the deionization step, and batch contacting with large excesses of reagents and long reaction times were common practice. The objective of the deionization step is to remove the alkaline and alkaline earth cations from the biomass and treatment methods which allow this to be done with a minimum of residual cations remaining in the biomass are preferred. Following the deionization step, we have found that it is not necessary to wash the biomass to remove residual acid as was practised in the prior art, as long as the cation contaminated acid has been substantially displaced by cation free acid solution. This represents an important economic advantage because washing to remove acid was done in the prior art using large quantities of deionized or distilled water, which is not necessary with the process of this invention. Further, the acid solution recovered from the treated biomass by draining, filtering, pressing or other means can be reused for new batches of untreated biomass. It has further been determined that certain anions can have a minor but beneficial effect in increasing yields of sugars, particularly levoglucosan, if they are present in the deionized wood. It appears that the preferred anions in order of descending efficacy are:

sulfate/phosphate/nitrate/sulfite/chloride/organic although the differences in behaviour are not large for the inorganic anions. These anions can be conveniently added to the deionized biomass as ammonium salts, as these salts decompose on pyrolysis and liberate ammonia so that no undesirable cations are introduced. Alternatively, if the acid is not washed out, as in an embodiment of this invention, then the anion of the acid used will remain in the biomass during pyrolysis with beneficial effects on the yield of sugars and anhydrosugars. For this reason it is preferred to use sulfuric or nitric acid, but any suitable acid may be used if there are economic or other advantages in doing so.

The deionized biomass can be pyrolyzed successfully with a wide range of moisture contents, for example, from 1% to 30% by weight, but for reasons of energy efficiency a moisture content range of 5% to 15% is preferred. It is a feature of this invention that the yields of sugars and anhydrosugars obtained at atmospheric pressure in a continuous fast pyrolysis reactor from deionized biomass or prehydrolyzed biomass are consistently higher than those reported in the prior art for pyrolysis at atmospheric pressure in small batch laboratory processes. In order to achieve similar yields in the prior art, it was necessary to operate under vacuum.

According to this invention, if biomass is deionized as described above so that the hemicellulose content is substantially unaffected, then a single fast pyrolysis step is sufficient to depolymerize both the hemicellulose and the cellulose content of the biomass with substantial yields of a variety of sugars and anhydrosugars derived from both the hemicellulose and cellulose fractions. For example, it has been found that in the pyrolytic liquids from the fast fluidized bed pyrolysis unit, and also from the up flow transport reactor according to the invention, not only is levoglucosan found as a major constituent but also anhydroxyloses if hardwood is used or anhydromannoses if softwood is used; this was not known in the prior art.

Unless the feed material has been previously delignified, for example a bleached wood pulp, it will contain essentially all of the lignin fraction of the wood after either an acid prehydrolysis or deionization.

It is important to appreciate that when the alkaline or alkaline earth cations have been removed, the nature of the thermal decomposition of the lignin also changes as does that of the hemicellulose and the cellulose. The products of this thermal decomposition process of lignin can cause operating problems in many of the presently used types of continuous fast pyrolysis reactors, a factor not understood in the prior art. It is an important feature of this invention that this lignin fraction, in the absence of alkaline or alkaline earth cations, can be selectively oxidized in fast pyrolysis by the controlled use of added air or oxygen, without affecting in any significant way the depolymerization processes of the hemicellulose and/or cellulose, and in particular without affecting significantly the yields of sugars or anhydrosugars. This is not the case for biomass which has not been pretreated to remove these anions. Oxidative pyrolysis, in untreated biomass, will affect yields of desirable chemicals not only by reducing the maximum amount of liquid product produced but also by specifically affecting yields of reactive components and of sugars and anhydrosugars. This is because of the effect of alkaline or alkaline earth cations in promoting oxidation reactions non-selectively, so that all fractions of the biomass are affected when undergoing pyrolysis if the biomass has not been pretreated to remove these cations.

The controlled selective oxidation of the lignin fraction of fast pyrolysis of pretreated biomass has several advantages in the production of sugar syrups from biomass by thermal methods. Normally, it is desirable to remove the lignin fraction from the pyrolytic liquids by some process such as the water extraction method described in U.S. Pat. No. 4,880,473, or by other extraction or chemical treatments. When oxidative pyrolysis is carried out at the proper conditions, the lignin content can be largely selectively destroyed and removed as oxidation products such as carbon dioxide, carbon monoxide or water. A second advantage is that the oxidation process is exothermic and this method of operation therefore can generate in situ much or all of the heat required by the endothermic depolymerization reactions of the hemicellulose and/or cellulose. A third advantage is obtained because the lignin during oxidation does not yield components which cause operating problems in the reactor and therefore reactor operation is simplified and more reliable. A fourth advantage of this discovery is that the pyrolytic liquids produced can be more concentrated in the desirable sugars and anhydrosugars because of the removal of the lignin fraction as non-condensable oxidation products. Of course, as with all organic oxidations carried out at elevated temperatures, proper precautions are necessary to ensure control of the rapid oxidation processes. The net benefit of this novel discovery is to allow a pyrolytic syrup containing anhydrosugars and sugars to be produced which is largely free of decomposition impurities derived from lignin and which is therefore easier and more economical to purify and which is more concentrated, and which has been produced in a more energy efficient and simpler way.

The liquid product from the pyrolysis of deionized biomass will contain only minor amounts of water-soluble components derived from the lignin fraction of the biomass after either the water extraction step in the case of non-oxidative pyrolysis, or as residual lignin-derived components in the case of oxidative pyrolysis. These components are primarily aromatic in character and can be readily removed by treatment with activated charcoal.

If a solution of anhydrosugars is desired, the pyrolysis liquid containing the sugars and anhydrosugars must be hydrolyzed to, for example, glucose, xylose, mannose, etc, for use in fermentation processes. This is well-known technology and is usually done by treatment with a mineral acid such as sulfuric or hydrochloric acid. Removal of the residual undesirable components derived from lignin can be accomplished using the activated carbon treatment either before or after hydrolysis of the anhydrosugars. Normally it would be preferable to purify the aqueous liquid before acid hydrolysis to prevent side reactions with the acid, but in cases where the amount of soluble aromatics is very small, activated carbon treatment may be carried out either before or after hydrolysis.

The liquid product from the fast pyrolysis step will normally be acidic and if it is stored for a long period, acid levels may be sufficiently high to cause some hydrolysis of the levoglucosan to glucose. Therefore, if it is desired to produce crystalline anhydrosugars, the pH may be adjusted to 4 to 5 which reduces the acidity to a level at which prolonged storage of the liquid or prolonged evaporation at higher temperatures can be done without loss of anhydrosugars due to hydrolysis. Any convenient base can be used for this neutralization step, such as lime, sodium hydroxide, ammonia etc.

After neutralization, if performed, the water and other volatiles are evaporated from the aqueous solution containing the anhydrosugars, preferably under vacuum at temperatures from 60° C. to 120° C., although evaporation can be carried out at atmospheric pressure with some loss of product. Water content should be reduced to less than 5% by weight and preferably to below 3%. If insufficient water is removed it is difficult to crystallize the levoglucosan in good yields. The essentially anhydrous residue is dissolved in hot alcohol, preferably anhydrous ethanol, using a weight ratio of alcohol to residue in the range of 0.5 to 2, although the exact ratio is not a critical factor. Methanol can also be used although crystallization is not as readily achieved from methanol. Propanol can also be used but the solubility of the residue in this solvent is limited. If any insoluble residue is evident, the alcoholic solution can be filtered. Some salts that may be formed in a neutralization step are only slightly soluble in alcohol, and these will precipitate and can be removed by filtration. The hot alcoholic solution is then preferably passed through a column of granular activated carbon to reduce carbon consumption. The decolorized alcoholic solution after treatment by the activated carbon is then evaporated until the concentration of the dissolved levoglucosan approaches a value of about 25% by weight (if ethanol is the solvent) and is then cooled in a crystallizing vessel, and crystals of levoglucosan will immediately appear when the saturation point is reached. The solution is cooled to 5° C. to 15° C. and then the crystals are separated from the mother liquor by filtration or by centrifuge and washed with cold alcohol. The mother liquor is reheated and solvent evaporated from it, and on further cooling additional crystals of levoglucosan are obtained. The above crystallization procedure has also been done using methanol but the solvent must be evaporated to give a higher concentration of levoglucosan before crystallization because of the greater solubility of levoglucosan in methanol.

In the processing step (f) in which water and other volatiles are evaporated to give a residue low in water content, it is of course possible to employ other methods of water removal such as azeotropic distillation using solvents such as ethanol, methyl isobutyl ketone, etc.

It is also apparent that if the crystals of levoglucosan obtained by the process described in this invention are not of sufficient purity or are discoloured, that a product of the desired degree of purity can be prepared by recrystallization from alcohol, preferably ethanol, by conventional techniques.

The procedure described as "fast pyrolysis" has been described previously in Canadian Pat. 1,241,541 and in U.S. Pat. 4,880,473. Fast pyrolysis occurs at atmospheric pressure in a reactor capable of high heat transfer rates such as a fluidized bed or transport reactor. Apparent residence times of volatiles are less than 10 seconds and are preferably in the range of 0.1 to 2.0 seconds. Temperatures are in the range of 400° C. to 650° C. When operated in a non-oxidative mode, any non-oxidizing gas can be used for conveying the biomass feed into, and the pyrolysis products from, the reactor, and commonly recycled product gas (noncondensables) is employed. In the non-oxidizing mode, a preferred temperature range for pyrolysis for most biomass is 450° C. to 550° C. When used in an oxidizing mode when some air or oxygen is added to the reactor gas flow, somewhat lower temperatures may be optimal, e.g. from 400° C. to 500° C.

BRIEF DESCRIPTION OF THE DRAWINGS

Flow sheets illustrating certain preferred embodiments of this invention are contained in FIGS. 1, 2 and 3.

Figure 1:
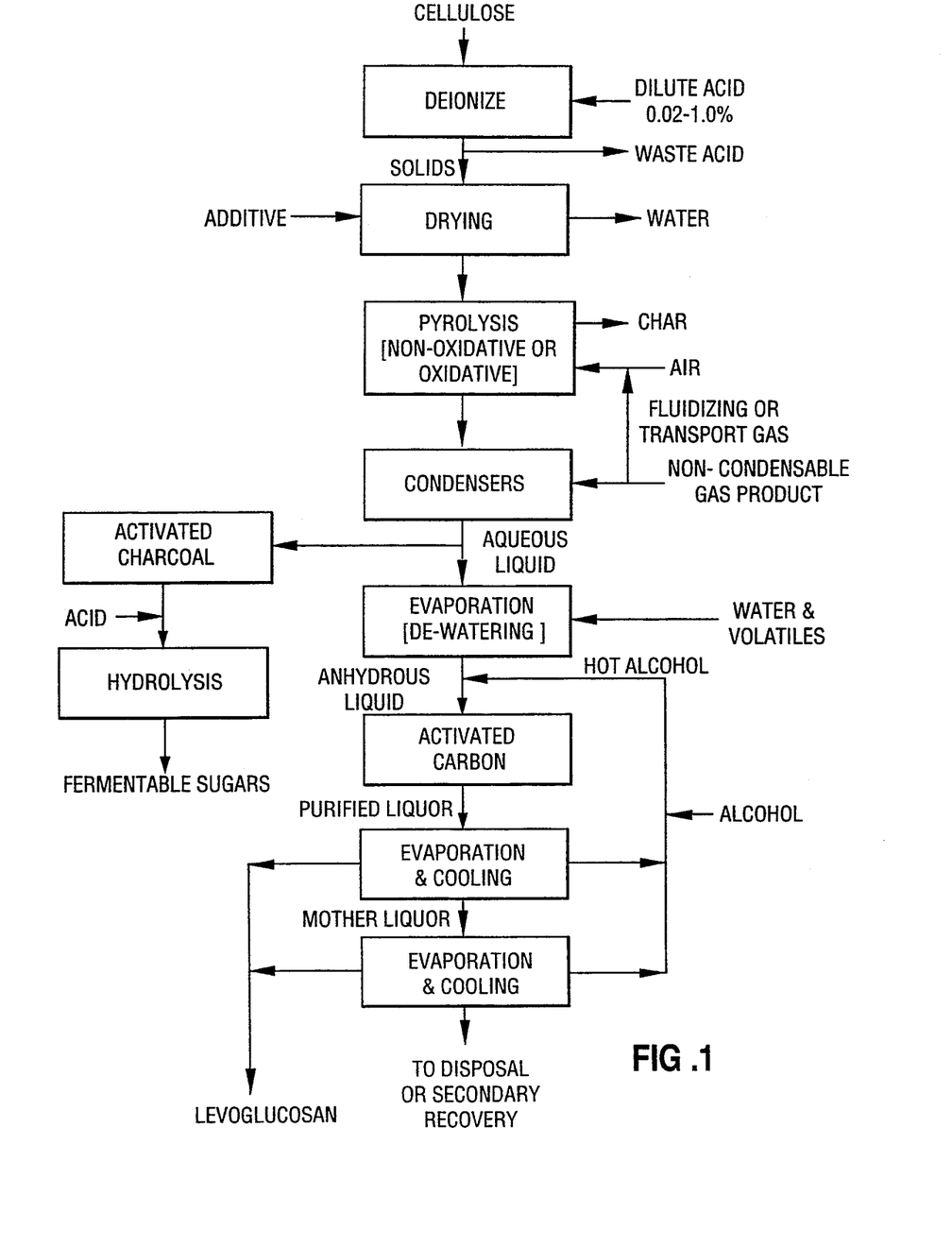
Figure 2:
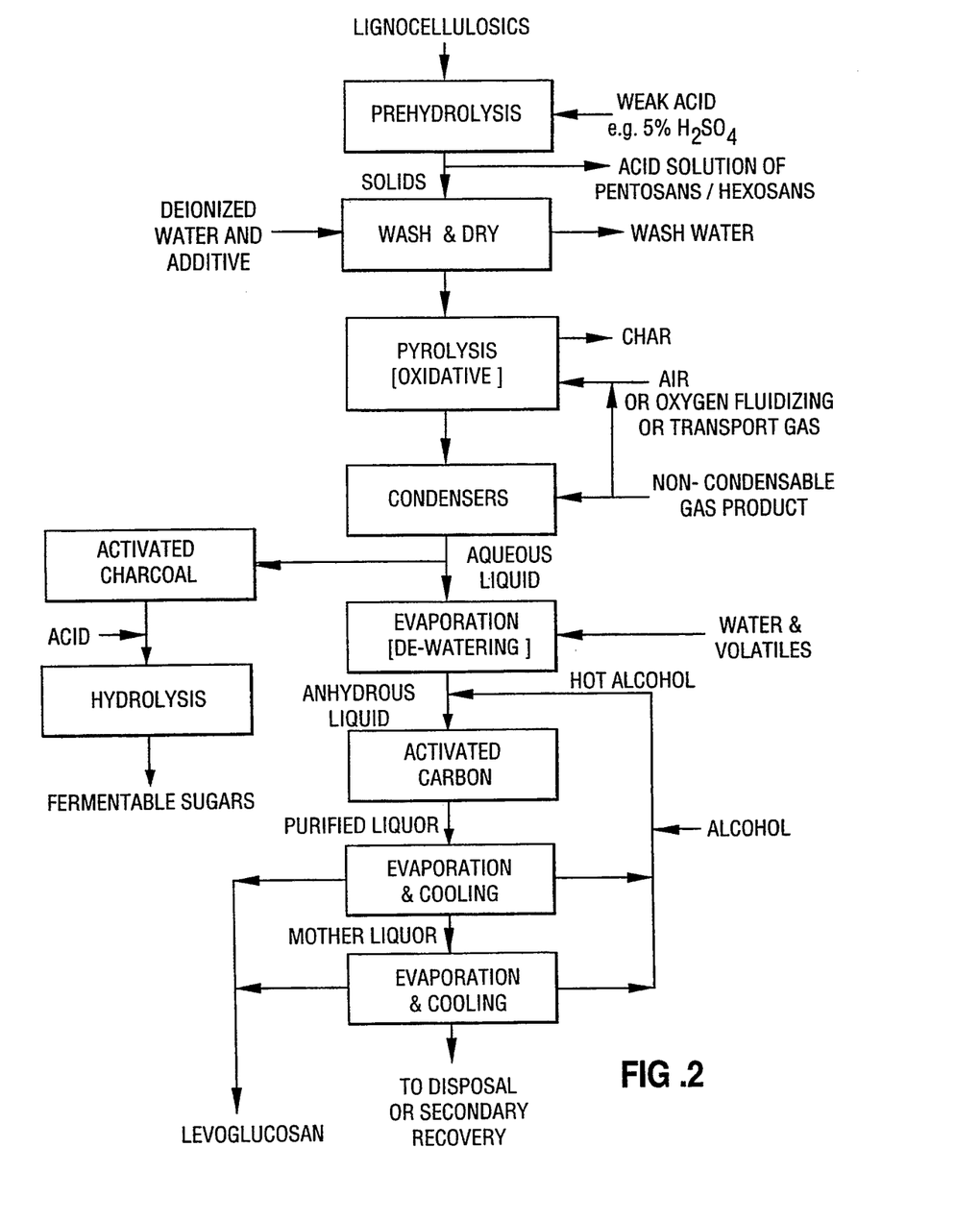

The processing schemes described above are shown in FIGS. 1, 2 and 3. The deionizing of the biomass is carried out as described above, (FIGS. 1 and 3) and the prehydrolysis procedure to remove hemicellulose and alkaline cations is carried out according to the description given in U.S. Pat. No. 4,880,473 except that now it may be also applied to biomass-derived substances such as newsprint or waste fibre or other waste lignocellulosics (FIGS. 2). When there is little or no lignin and hemicellulose present in the feed material, such as in the case of wood pulp or some papers, and it is desired to produce anhydrosugars, then the part of the processing scheme shown as FIG. 1 is used which consists of deionization followed by non-oxidative fast pyrolysis, treatment of the pyrolysis liquid with activated carbon and then acid hydrolysis of the liquid. As examples of suitable fast pyrolysis reactors, the inventors have used successfully with deionized celluloses both fluidized beds and transport reactors at the conditions specified in U.S. Pat. No. 4,880,473. The final aqueous solution consists primarily of glucose with a concentration of up to 300 grams per liter depending on the feed moisture content, hydrolysis conditions, and operating methods used. If it is desired to produce crystalline anhydrosugars e.g. levoglucosan, then the part of FIG. 1 which prepares an anhydrous residue from the fast pyrolysis liquid is followed. This process has been used with pretreated wood pulp and with waste paper or cellulosic fibre to prepare anhydrous residues according to FIG. 1, from which levoglucosan can be recovered.

When a biomass feedstock contains lignin, hemicellulose and cellulose, then either of two pretreatment schemes may be used. In FIG. 2 is shown the process flowsheet for a prehydrolysis pretreatment essentially as described in U.S. Pat. No. 4,880,473. However, the fast pyrolysis step is now carried out using the present invention, by controlled partial oxidative fast pyrolysis. Reaction conditions are the same as used for non-oxidative pyrolysis except that controlled amounts of air or oxygen are added to the recycle product gas or flue gas used in the fluidized bed, transport reactor or other fast pyrolysis reactor and a slightly lower operating temperature, in the preferred range of 400° C. to 500° C., is optimal. For ordinary biomass such as hardwoods or softwoods, it has been found that oxygen concentrations of 2% to 21% (i.e. air) in the fluidizing or transport gas can be used. However, control of the oxidation rate is difficult at the higher oxygen concentrations and the preferred range of oxygen concentration in the inlet gas is in the range of 2% to 15% by volume. The oxygen input should be in excess of the stoichiometric requirement for oxidation of the lignin content of the pretreated biomass to carbon dioxide and water, and for the gas residence times used in fast pyrolysis this would require about 0% to 200% excess oxygen, depending on the reactivity of the lignin fraction of the biomass species used as feedstock. The resulting pyrolysis liquid contains from 0% to about 5% pyrolytic lignin, depending on the temperature used and the oxygen concentration. It is preferable to use reaction conditions that minimize the amount of residual lignin-derived products in the pyrolytic liquor. Because of the exothermic nature of the oxidation reaction, it has been found that lower reaction temperatures can be used in oxidative pyrolysis, and for a high degree of oxidation of the lignin fraction a temperature range of 400° C. to 500° C. is preferred with an oxygen content in the inlet gas of 10% to 15%. Above 500° C. good yields of anhydrosugars can still be obtained, but the yield will decrease with increasing temperatures. At the preferred conditions, residual pyrolytic lignin will be in the range of 0% to 3% by weight of the dry feed.

If the resulting pyrolytic liquor is to be used as a source of anhydrosugars, it can be treated with activated carbon to remove residual lignin-derived aromatic components either before or after acid hydrolysis. The aqueous acidic solution will contain primarily glucose at concentrations which can be as high as 500 grams per liter but will more commonly be in the range of 50 to 300 grams per liter depending on the type of biomass used and its moisture content as well as on the hydrolysis conditions used.

If the pyrolytic liquid obtained by the process shown in FIG. 2 is to be used as a source of crystalline anhydrosugars, then after removal of water and volatiles and dissolution of the residual tars in alcohol, the solution is treated with activated carbon to remove undesirable components, largely aromatic in character, which are derived mainly from the lignin fraction of the biomass. The activated carbon will also remove many other impurities which may derive from the carbohydrate fractions of the biomass, such as coloured components of high molecular weight and carbohydrate derived carboxyl compounds, acids, esters and lactones. Anhydrosugars are then crystallized from the purified alcoholic solutions.

Figure 3:
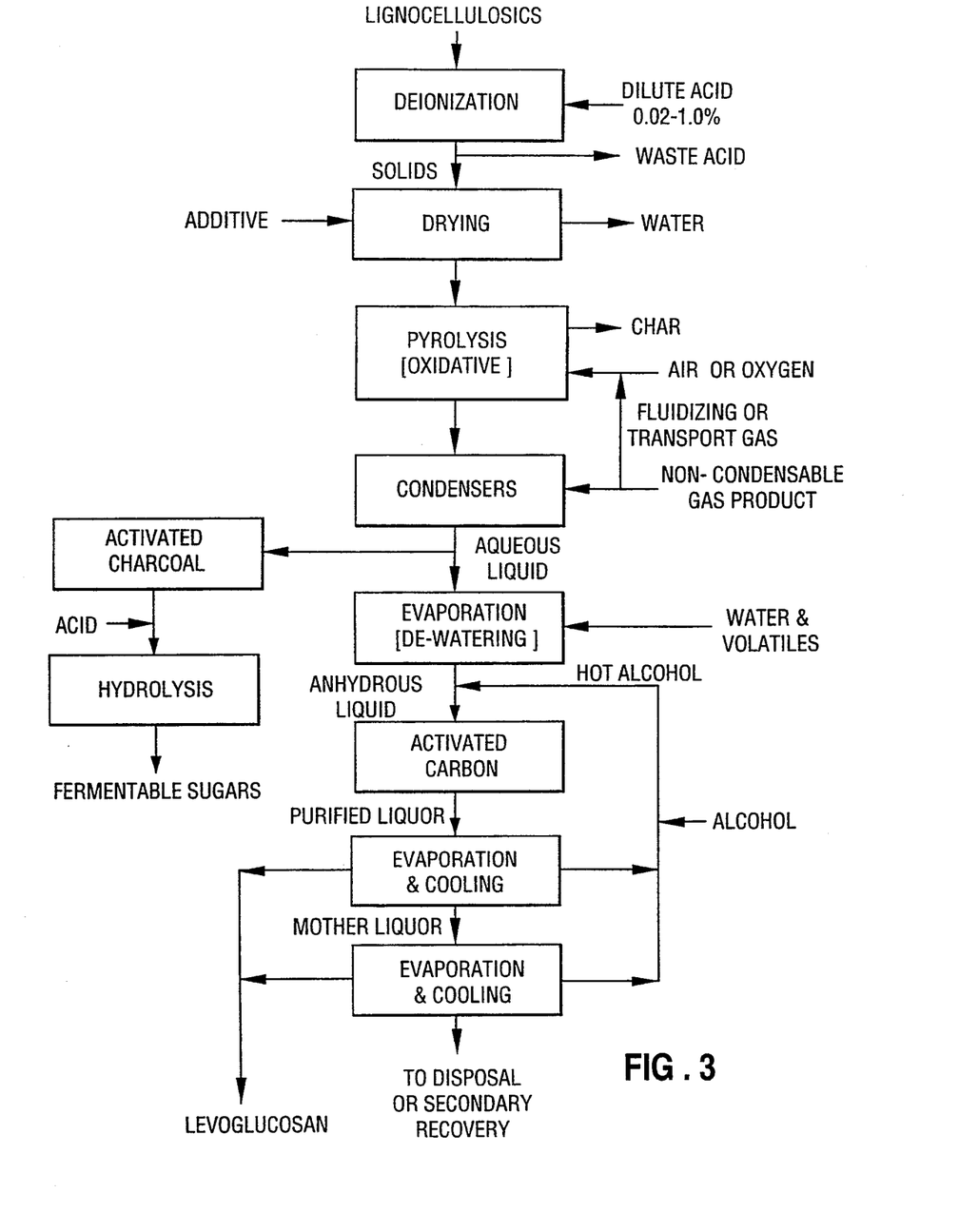

In FIG. 3 is shown a process flow sheet for in biomass containing lignin, hemicellulose and cellulose fractions which is first deionized as described earlier and then without further washing to remove dilute acid is dried to a moisture content below 30% and then pyrolyzed in a fast pyrolysis reactor under conditions of partial oxidation achieved by the addition of air or oxygen to the fluidizing or transport gas which is normally recycled product gas or flue gas. In the schemes shown in both FIGS. 2 and 3, there may not be present sufficient anion of the desired type due to excessive washing as in Flowsheet B or due to the dilution of the acid or its type in the FIG. 3. It has been found convenient to add the desired anion (usually sulfate, sulfite or nitrate) by addition of the appropriate ammonium salt to the amount of 0.01% to 0.5% of the dry weight of the biomass feed by impregnation of the biomass after deionizing with a more concentrated solution of the salt.

In FIG. 3, pyrolysis of the dried deionized biomass is carried out as described for FIG. 2. The aqueous pyrolysis liquor is purified over activated charcoal as described for FIG. 2 if it is desired to prepare solutions of anhydrosugars. The resulting sugar syrup will contain not only glucose as the largest single component but also other hexoses and pentoses derived from the hemicellulose content of the biomass with total reducing sugar contents of 50 to 300 grams per liter when using common biomass materials such as wood as feed. The fermentation characteristics of these solutions will differ from those of solutions obtained by use of FIGS. 1 and 2 because of the presence of appreciable amounts of non-glucose sugars.

It has been found in laboratory tests that the sugar syrups obtained from the processes shown in FIGS. 1 and 2 can be readily fermented (after pH adjustment and necessary nutrient additions) rapidly and completely by baker's yeast to give a solution of ethanol. Sugar syrups obtained from deionized biomass as in FIG. 3 will require additional special cultures to efficiently ferment the pentose constituents. It is an improvement of the conversion of cellulose to glucose by the methods described here that sugar solutions can be readily obtained which are much more concentrated than those normally obtained by strong acid or enzymatic methods.

If the pyrolysis liquid prepared by FIG. 3 is to be used as a source of crystalline anhydrosugars, then the liquid is subjected to water removal, solution of the anhydrous residue in alcohol, purification of the alcoholic solution with activated charcoal and crystallization of the levoglucosan or other anhydrosugar from the alcoholic solution, as described above. However, in the case of pyrolysis liquids prepared by FIG. 3, the final purified alcoholic solution will also contain significant quantities of other anhydrosugars, mainly derived from the hemicellulose fraction of the biomass, which is also depolymerized with little loss of anhydrosugar yield during oxidative pyrolysis according to this invention. These other kinds of anhydrosugars may be recovered, after removal of much of the levoglucosan as described above, from the mother liquor remaining by the application or well-known techniques of fractional crystallization.

It is a feature of this invention that none of the three processing schemes shown in FIGS. 1, 2 and 3 require an extraction step for the removal of lignin-derived pyrolysis components of the liquid product such as was used in U.S. Pat. No. 4,880,473, or in processes such as those of Peniston, U.S. Pat. No. 3,374,222 or of Esterer, U.S. Pat. No. 3,309,356. This result is achieved by using a feedstock from which the lignin fraction has already been removed, or by removal during pyrolysis of the lignin contained in the prehydrolyzed or deionized biomass by selective oxidation by the process disclosed in this invention.

The process of the invention is further illustrated by the following examples.

EXAMPLE 1

A commercial cellulose prepared from bleached wood pulp containing 99+% cellulose and 0.22% ash containing alkaline cations was washed with hot 5% sulfuric acid to deionize it. After washing with deionized or distilled water to an effluent pH of 2 to 4, the deionized cellulose was dried to 4.0% moisture and pyrolyzed in a fluidized bed of sand operating continuously at atmospheric pressure and 500° C. The fluidizing gas was nitrogen (non-oxidizing), and the apparent residence time of volatiles was 0.46 seconds. A similar test was done using a sample of the cellulose which had not been deionized. Liquid yields were 84% of the feed for the untreated cellulose and the liquid contained 16% of anhydrosugars and sugars. The deionized cellulose gave a yield of 90% liquid which contained 51.4% anhydrosugars and sugars with levoglucosan (1,6-anhydro-B-D-glucopyranose) being two thirds of the total sugar content. This test corresponds to the processing scheme of Flowsheet A and illustrates the negative effect of the alkaline cations on the depolymerization reactions of cellulose which yield levoglucosan.

The pyrolytic liquid obtained from the high quality cellulose feed had a water content of 26.7% by weight. A sample was de-watered by evaporation under vacuum at a temperature of 60° C. to 70° C. The de-watered residual tar contained 54.4% levoglucosan vs. 56% calculated, as well as 11.4% anhydroglucofuranose and 2.2% cellobiosan, showing essentially no loss of levoglucosan on evaporation even without pH adjustment. Other samples were de-watered by azeotropic distillation, one with ethanol and one with methyl isobutyl ketone, with equivalent results. Methanol was used to dissolve 443.4 g of the tar in 200 g of solvent. The solution was cooled slowly to 5° C. and left standing. A yield of 130.4 g of brown crystals analysing over 90% levoglucosan was obtained. The filtrate was concentrated by evaporation of the methanol until the levoglucosan concentration was 28%. The solution was again cooled to 5° C. and allowed to stand. A further yield of crystals of 72.2 g was obtained giving a total recovery of 84% of the original content of levoglucosan.

EXAMPLE 2

A sample of 50 g of the de-watered tar prepared in example 1 was dissolved in 100 ml. of hot ethanol (70° C.), and cooled slowly at a linear rate in two hours to 15° C. 25.8 g of pale yellow crystals of levoglucosan were obtained with a yield of over 90%.

EXAMPLE 3

A sample of 50 g of crude de-watered product prepared in example 1 in 100 ml of hot (70° C.) ethanol and 25 g of activated carbon added to the solution which was then kept for several hours at 60° C. with stirring and then filtered. The filtrate was water white. The alcohol solvent was evaporated from the solvent at 65° C. until the concentration of levoglucosan reached 25% at which point crystallization of levoglucosan began. The evaporation continued while the solution was cooled to 25° C., and was carried out nearly to dryness, 25 g of fine white crystalline levoglucosan (M.P. 180°–182° C.) was recovered.

EXAMPLE 4

A sample of hybrid poplar wood was prehydrolyzed using 5% sulfuric acid at 900° C. for two hours to remove most of the hemicellulose and essentially all of the alkaline cations. After washing with deionized water to remove most of the sulfuric acid, the biomass was dried to 4.0% moisture and then pyrolyzed in a small pilot plant fluidized sand bed reactor at atmospheric pressure and an average temperature of 400° C. with an apparent gas residence time of 0.68 seconds. The fluidizing gas was a mixture of nitrogen, steam and air to give an oxygen content in the inlet fluidizing gas of 14.5% by volume and was at a volumetric flowrate sufficient to give 55% excess of oxygen over the stoichiometric requirement for complete lignin oxidation. Pretreated poplar wood was fed continuously at a rate of 1.23 kg/hr. The liquid product contained about 5% lignin-derived products, representing about 15% of the lignin originally fed in the pretreated wood, and also contained 35% anhydrosugars. This aqueous liquid product, after treatment with activated carbon to remove residual lignin-derived components, can be hydrolyzed to glucose and other sugars for fermentation. For comparison, a similar pyrolysis test with untreated poplar wood gave a liquid which contained only 11% anhydrosugars and sugars. After evaporation of the water and volatiles the levoglucosan content was 35 to 40% of the residual tar. The tar was dissolved in ethanol and the pH adjusted by the addition of lime in aqueous solution. The ethanol-water solution was filtered and concentrated by evaporation to 70% solids. No levoglucosan crystallized because of the water content. To 50 g of this concentrated solution 120 g of ethanol was added and 25 g of activated charcoal and the solution was stirred at 65° C. for five hours. The purified solution was then evaporated and 11 g of levoglucosan was recovered (estimated recovery 63%).

EXAMPLE 5

The results obtainable by oxidative pyrolysis of wood are given in this example. A softwood (western hemlock) with a maximum particle size (smallest dimension) of 0.5 mm was used as feedstock. 1.4 kg of sawdust was slurried with 0.1% by weight sulfuric acid solution and pumped into a column 10 cm diameter and 122 cms long. 17 liters of 0.1% acid solution were then percolated slowly through the column at 20° C. at a rate of 50 ml/min. The wood was then drained and dried to yield 1.356 kg of deionized feedstock. This pretreated wood was then subjected to fast pyrolysis at both non-oxidizing and oxidizing conditions. Results of these tests are shown in Table 1. Run 78 shows the pyrolysis results with no pretreatment of the hemlock, indicating the poor yields of levoglucosan obtained. Run 74 shows results for pyrolysis of deionized hemlock wood. Run 99 shows results for the pyrolysis of untreated hemlock in an oxidizing mode in the pyrolysis reactor. Run 97 gives the results for deionized hemlock with 0.1% of ammonium sulfate added and pyrolyzed in the oxidative mode at the same temperature as Run 99.

It is apparent from the results in this table that in deionized wood the lignin can be selectively oxidized in the fast pyrolysis reactor with essentially no effect on the yield of levoglucosan obtained.

EXAMPLE 6

The effect of temperature is shown in Table 2 for oxidative pyrolysis of a deionized western hemlock sawdust in a fluidized bed reactor with an oxygen concentration in the inlet gas of about 12% by volume. Another test, Run 86, done with no oxygen in the inlet gas, is shown also. By comparison of Run 97 and 86, both done at the same temperature, it is apparent that yields of levoglucosan are not affected adversely by the use of partial oxidation, but that the amount of pyrolytic lignin appearing in the pyrolysis liquid is reduced to a low value by the use of these oxidizing conditions. Run 96 at 410° C. and Run 97 at 455° C. give very comparable results and both show only small residual amounts of pyrolytic lignin in the liquid product while the levoglucosan yield is unaffected. The yield of most liquid components, but particularly the levoglucosan yield, is seen to be reduced in Run 98, done at 510° C., while the non-condensable gas yield is considerably increased. This demonstrates the less selective nature of the oxidation processes at higher pyrolysis temperatures.

EXAMPLE 7

The effect of using air only as the fluidizing or transport gas is shown in Table 3 for three types of deionized feedstocks, a hardwood, an unbleached wood pulp and a waste cellulosic sludge from a paper mill. When air alone is used (oxygen content 21% by volume), temperature of pyrolysis has a strong effect on extent of the oxidation reactions. Although the yields of levoglucosan and sugars are reduced by the use of these high oxygen levels, the amounts of other soluble products, particularly those derived from lignin, are also significantly reduced. Clearly, an optimal set of conditions of temperature and oxygen content exist, which will be determined largely by feedstock value and by the reduction in operating and recovery problems obtained when oxidative pyrolysis is used.

The results for the poplar wood show the beneficial effect in reduction of lignin-derived products in the pyrolysis liquids which can be obtained by oxidative pyrolysis. In non-oxidizing atmospheres (e.g. see Table 1), the normal yield of lignin-derived components in the pyrolysis oil is 20% to 30% depending on the feedstock and temperature. This can be reduced by at least 50% or more depending on the temperature with much less severe losses of levoglucosan yield. Better results can usually be obtained with somewhat lower oxygen content in the fluidizing or transport gas.

Results in Table 3 also show that it is not necessary to wash out the weak acid used for the deionization process in order to obtain good yields of anhydrosugars. The major effect of this more economical processing method appears to be an increase in char yield.

EXAMPLE 8

The results given in Table 4 show the effect of increasing levels of oxygen in the fluidizing or transport gas on the yields of the important products for the fast pyrolysis of a prehydrolyzed hardwood (poplar). It is evident that the yield of organic liquid decreases somewhat as the oxygen level increases, but the composition of the total liquid is much less affected. The total liquid yields (organic liquid plus water) are nearly constant for the oxidative runs and vary only from 85% to 87% for the runs at 436° C. and at 460° C. It is apparent, therefore that the quantity of levoglucosan produced is nearly constant in spite of the increasing degrees of oxidation occurring as oxygen level increases, as shown by the increased yield of gas and water. However, the yield of volatile organics derived from lignin—the "pyrolytic lignin"—is reduced to about 50% or less of that produced in non-oxidative pyrolysis of prehydrolyzed poplar. Although the hardwood lignin appears to be more difficult to oxidize than softwood lignin components, it is apparent that conditions can be found which will yield a maximum reduction in these lignin-derived volatiles while preserving the great majority of the yield of anhydrosugars, particularly levoglucosan.

TABLE 1

| Pyrolysis of Western Hemlock Sawdust 0.5 seconds residence, Temperature 450–490° C. | | | | |
| --- | --- | --- | --- | --- |
| Run No. | 78* | 74** | 99* | 97* |
| Feedstock | Untreated wood | Deionized wood | Untreated wood | Deionized wood |
| Atmosphere | Nitrogen | Nitrogen | N2 + air | N2 + air |
| % Oxygen in gas | 0 | 0 | 12 | 12 |
| Yields, wt % mf. feed | | | | |
| Gas | 12.0 | 5.1 | 68.0 | 40.5 |
| Product water | 9.4 | 9.5 | 27.5 | 18.2 |
| Organic liquid | 56.5 | 64.7 | 32.3 | 54.8 |
| Char | 18.2 | 17.3 | 12.7 | 13.3 |
| Total | 96.1 | 96.6 | 140.5 | 126.8 |
| Liquid composition, wt. % | | | | |
| Levoglucosan | 2.5 | 16.8 | 1.3 | 18.7 |
| Cellobiosan | 0.5 | 2.5 | 0.0 | 3.4 |
| Hydroxyacetaldehyde | 10.6 | 2.2 | 3.2 | 2.1 |
| Anhydromannoses | 0.0 | 5.2 | 0.0 | 10.6 |
| Formaldehyde/formic acid | 4.0 | 0.0 | 4.8 | 0.0 |
| Acetic acid | 1.4 | 1.6 | 1.0 | 0.0 |
| Acetol | 3.4 | 0.0 | 0.0 | 0.0 |
| Pyrolytic lignin | 19.9 | 21.6 | 3.4 | 1.5 |

*Fluidized Bed
**Transport Reactor

TABLE 2

Effect of Temperature in Selective Oxidation of Lignin
0.5 seconds residence time, fluidized bed, 5% moisture

| Run No. | 96 | 97 | 98 | 86 |
|---|---|---|---|---|
| Temperature, °C. | 410 | 455 | 510 | 455 |
| % Oxygen in Gas | 12.9 | 12.1 | 11.5 | 0 |
| Yields, % mf. feed | | | | |
| Gas | 39.0 | 40.5 | 67.8 | 4.4 |
| Product water | 20.6 | 18.2 | 25.3 | 7.0 |
| Organic liquid | 47.7 | 54.8 | 45.1 | 69.1 |
| Solid residue (char) | 21.5 | 13.3 | 4.3 | 16.1 |
| Total | 128.8 | 126.8 | 142.5 | 96.6 |
| Liquid Composition, wt. % | | | | |
| Cellobiosan | 1.4 | 3.3 | 2.1 | 5.2 |
| Levoglucosan | 18.8 | 18.7 | 12.6 | 15.8 |
| Hydroxyacetaldehyde | 1.8 | 2.1 | 0.0 | 3.1 |
| Anhydromannose | 10.9 | 10.6 | 9.0 | 9.0 |
| Acetic acid | 0.0 | 0.0 | 0.0 | 0.0 |
| Pyrolytic lignin | 0.0 | 1.5 | 2.7 | 14.2 |
| % Sugars in liquid | 31.1 | 32.6 | 23.7 | 30.0 |

TABLE 3

Comparison of Fast Pyrolysis in Air and Inert Atmospheres
Fluid Bed, Residence Time 0.5 seconds, Deionized Feeds

| Feedstock | Unbleached Wood Pulp* | Poplar | Poplar + Additive | | Paper Mill Sludge* | | |
|---|---|---|---|---|---|---|---|
| Temperature, °C. | 420 | 495 | 445 | 495 | 450 | 440 | 510 |
| Atmosphere | Nitrogen | Nitrogen | Air | Air | N$_2$ | Air | Air |
| Yields, wt. % mf feed | | | | | | | |
| Gas | 2.3 | 8.4 | 45.1 | 74.5 | 5.3 | 45.9 | 67.1 |
| Product Water | 13.0 | 7.5 | 25.5 | 31.2 | 11.0 | 26.9 | 30.4 |
| Organic Liquid | 71.2 | 76.4 | 55.4 | 39.0 | 64.8 | 44.0 | 36.7 |
| Char | 10.2 | 4.7 | 6.2 | 1.8 | 18.2 | 13.0 | 7.0 |
| Total | 96.7 | 97.0 | 132.2 | 146.5 | 99.322 | 129.8 | 141.2 |
| Liquid Composition % by wt. | | | | | | | |
| Levoglucosan | 30.3 | 9.8 | 17.6 | 9.8 | 30.1 | 21.5 | 12.6 |
| Other anhydrosugars | 12.4 | 10.5 | 7.9 | 5.1 | 13.8 | 5.7 | 2.2 |
| Hydroxyacetaldehyde | 1.0 | 5.9 | 0.0 | 0.0 | 1.9 | 0.0 | 0.0 |
| Glyoxal | ND | 3.9 | 2.9 | 3.4 | 0.0 | 1.0 | 2.0 |
| Acetic acid | 0.0 | 1.3 | 1.4 | 1.3 | 0.0 | 0.0 | 0.0 |
| Lignin-derived tars | 9.0 | 16.9 | 12.1 | 6.1 | 6.0 | 3.7 | 5.4 |

*Acid not washed out

TABLE 4

Fast Pyrolysis of Prehydrolyzed Poplar Wood
Fluidized bed, 0.50 seconds, 5.8% moisture

| Temperature, °C. | 501 | 436 | 460 | 460 | 460 | 500 |
|---|---|---|---|---|---|---|
| Atmosphere | N$_2$ + Air | N$_2$+ Air | N$_2$ + Air | N$_2$ + Air | Air | Air |
| % Oxygen in Gas | 0 | 1.6 | 6.0 | 12.3 | 21.0 | 21.0 |
| Yields, wt. % mf feed | | | | | | |
| Gas | 4.4 | 8.7 | 28.3 | 36.0 | 40.7 | 53.8 |
| Product water | 10.1 | 12.3 | 15.3 | 19.1 | 19.3 | 22.7 |
| Organic liquid | 77.0 | 68.2 | 64.3 | 62.8 | 61.0 | 51.8 |
| Char | 6.2 | 14.0 | 10.0 | 6.9 | 8.2 | 6.4 |
| Total | 97.7 | 103.2 | 118.0 | 124.7 | 129.2 | 134.8 |
| Liquid Composition, wt. % | | | | | | |
| Levoglucosan | 27.6 | 23.2. | 28.6 | 26.5 | 25.7 | 22.4 |
| Cellobiosan | 4.0 | 1.6 | 2.3 | 1.9 | 1.4 | 2.1 |
| Hydroxyacetaldehyde | 1.7 | 0.0 | 0.0 | 0.0 | 0.0 | 0.0 |
| Glucose | 0.0 | 0.0 | 3.6 | 1.8 | 2.4 | 2.6 |
| Glyoxal | 0.7 | 2.2 | 2.1 | 1.8 | 1.4 | 2.6 |
| Anhydrofuranose | 2.1 | ND | 3.8 | 5.3 | 3.9 | 3.0 |
| Formaldehyde/formic | 0.0 | 4.7 | ND | 6.5 | ND | 5.1 |
| Acetic acid | 0.0 | 0.0 | 0.0 | ND | ND | ND |
| Pyrolytic Lignin | 25.5 | 4.7 | 11.9 | 13.5 | 13.3 | 10.6 |

We claim:

1. A process for the production of anhydrosugars from cellulose-containing biomass, which comprises;
   (a) treating lignin and cellulose-containing biomass with a mineral acid having a concentration in the range of 1% to 10% by weight whereby hemicellulose is dissolved and alkali and alkaline earth cations are removed from the biomass while cellulose and lignin are not dissolved,
   (b) separating a cellulose and lignin-containing solid phase,
   (c) subjecting the resulting solid phase to rapid pyrolysis at atmospheric pressure, a temperature in the range of 400° C. to 650° C., a residence time of pyrolytic vapors of less than 10 seconds and in the presence of excess oxygen sufficient to completely oxidize lignin contained in the biomass feedstock, to thereby obtain a crude product containing anhydrosugars and
   (d) isolating the anhydrosugars as a product.

2. A process as claimed in claim 1 wherein the mineral acid is sulfuric acid.

3. A process as claimed in claim 2 wherein the biomass is contacted with the sulfuric acid at 70° C. to 100° C. for 2 to 6 hours.

4. A process as claimed in claim 2 wherein the rapid pyrolysis is carried out at a temperature in the range of 400° C. to 500° C.

5. A process as claimed in claim 2 wherein the rapid pyrolysis is carried out in the presence of excess oxygen sufficient to completely oxidize lignin contained in the biomass feedstock.

6. A process as claimed in claim 5 wherein an oxygen containing gas having an oxygen content of 2 to 21% is fed to the rapid pyrolysis.

7. A process as claimed in claim 6 wherein the oxygen content is 2% to 15%.

8. A process as claimed in claim 5 which includes the steps of removing water and other volatiles from the crude pyrolysis liquid to obtain a substantially anhydrous residue, dissolving the anhydrous residue in hot alcohol, treating the hot alcohol solution with activated carbon, and evaporating the alcohol to form crystals of levoglucosan.

9. A process as claimed in claim 1 wherein the anhydrosugars obtained are hydrolyzed to form fermentable sugars.

10. A process for the production of anhydrosugars from lignin- and cellulose-containing biomass, which comprises:
(a) treating lignin- and cellulose-containing biomass with a dilute acid at a concentration in the range of 0.05 to 1.0% by weight whereby alkali and alkaline earth cations are removed from the biomass while lignin, cellulose and hemicellulose are not dissolved,
(b) separating a lignin, cellulose and hemicellulose-containing solid phase,
(c) subjecting the resulting solid phase to rapid pyrolysis at substantially atmospheric pressure, a temperature in the range of 400° C. to 650° C., a residence time of pyrolytic vapours of less than 10 seconds and in the presence of excess oxygen sufficient to completely oxidize lignin contained in the biomass feedstock, to thereby obtain a crude pyrolysis liquid containing anhydrosugars and
(d) isolating the anhydrosugars as a product.

11. A process as claimed in claim 10 wherein the dilute acid is a dilute mineral acid.

12. A process as claimed in claim 11 wherein the acid is sulfuric acid.

13. A process as claimed in claim 11 wherein the rapid pyrolysis is carried out with a residence time of pyrolytic vapours of less than 2 seconds.

14. A process as claimed in claim 13 wherein the sulfuric acid has a concentration of 0.05% by weight.

15. A process as claimed in claim 13 wherein the solid phase fed to the rapid pyrolysis has particle sizes of less than 5 mm.

16. A process as claimed in claim 13 which includes the steps of removing water and other volatiles from the crude pyrolysis liquid to obtain a substantially anhydrous residue, dissolving the anhydrous residue in hot alcohol, treating the hot alcohol solution with activated carbon, and evaporating the alcohol to form crystals of levoglucosan.

17. A process as claimed in claim 13 wherein the anhydrosugars obtained are hydrolyzed to form fermentable sugars.

18. A process as claimed in claim 13 wherein an oxygen containing gas is fed to the rapid pyrolysis having an oxygen content of 2 to 11%.

19. A process as claimed in claim 18 wherein the oxygen content is 2% to 15%.

* * * * *